(12) United States Patent
Pellis

(10) Patent No.: US 8,864,689 B2
(45) Date of Patent: Oct. 21, 2014

(54) DEVICE FOR KNEE EVALUATION AND RELATIVE BRACE

(76) Inventor: Jacqueline Pellis, San Floriano del Collio (IT)

( * ) Notice: Subject to any disclaimer, the term of this patent is extended or adjusted under 35 U.S.C. 154(b) by 286 days.

(21) Appl. No.: 13/435,615

(22) Filed: Mar. 30, 2012

(65) Prior Publication Data

US 2012/0253235 A1    Oct. 4, 2012

(30) Foreign Application Priority Data

Mar. 30, 2011   (IT) .............................. GO2011A0003

(51) Int. Cl.
| | |
|---|---|
| A61F 5/00 | (2006.01) |
| A61B 5/103 | (2006.01) |
| A61B 5/117 | (2006.01) |
| A61B 5/00 | (2006.01) |
| A61B 5/107 | (2006.01) |
| A61F 5/01 | (2006.01) |

(52) U.S. Cl.
CPC ....... *A61B 5/4585* (2013.01); *A61F 2005/0146* (2013.01); *A61F 5/0123* (2013.01); *A61B 5/1071* (2013.01); *A61B 5/6828* (2013.01)
USPC .............................. 600/595; 600/587; 602/26

(58) Field of Classification Search
USPC ................................ 600/587, 595; 602/16, 26
See application file for complete search history.

(56) References Cited

U.S. PATENT DOCUMENTS

| | | | |
|---|---|---|---|
| 4,643,176 A | | 2/1987 | Mason et al. |
| 5,107,824 A | * | 4/1992 | Rogers et al. .................... 602/16 |
| 5,330,418 A | * | 7/1994 | Townsend et al. .............. 602/26 |
| 5,632,725 A | * | 5/1997 | Silver et al. ..................... 602/26 |
| 5,792,077 A | * | 8/1998 | Gomes .......................... 600/595 |
| 5,827,208 A | * | 10/1998 | Mason et al. .................... 602/16 |
| 2001/0056012 A1 | | 12/2001 | Pellis |
| 2005/0148916 A1 | | 7/2005 | Nathanson |
| 2006/0247565 A1 | | 11/2006 | Cormier et al. |

FOREIGN PATENT DOCUMENTS

| | | |
|---|---|---|
| EP | 0361405 | 4/1990 |
| WO | 8403433 | 9/1984 |
| WO | 9215264 | 9/1992 |
| WO | 9738759 | 10/1997 |

\* cited by examiner

*Primary Examiner* — Max Hindenburg
*Assistant Examiner* — Jonathan M Foreman

(57) ABSTRACT

A device for evaluating motion of a knee and for forming a brace which includes a first plate having four holes therein, a femoral arm, a tibial arm formed with a rectangular portion from which extends to a semi-circular portion having a central opening and an arcuate opening which for a first 25-30 degrees is an arc of a circle, for a subsequent 105-110 degrees is a spiral and is an arc of a circle from 135-140 to 180 degrees, a second plate having five holes therein and a small circular plate having a linear scale centrally thereof, a graduated arcuate scale and another arcuate opening configured to overlap the arcuate opening of the semi-circular portion of the tibial arm.

4 Claims, 12 Drawing Sheets

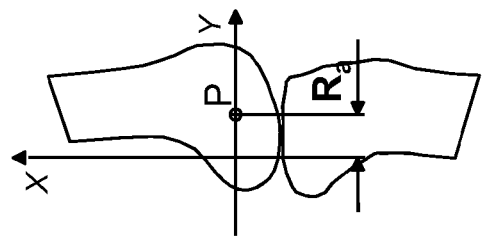
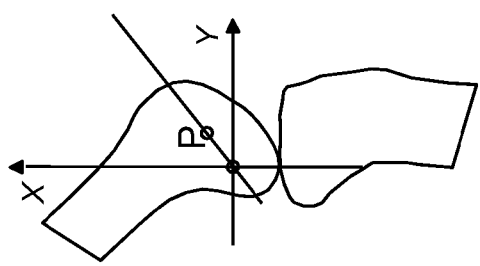
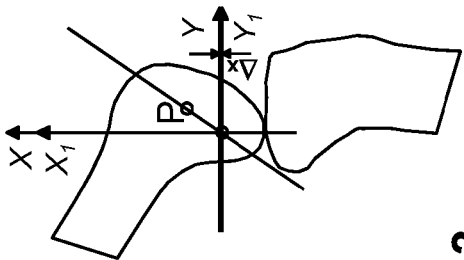
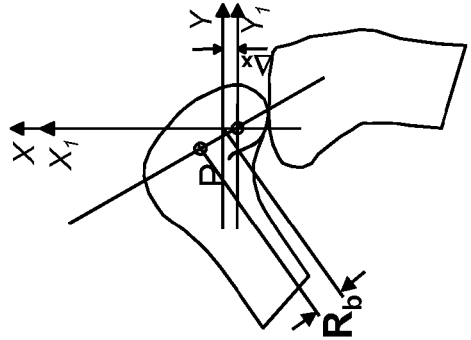
Fig. 3
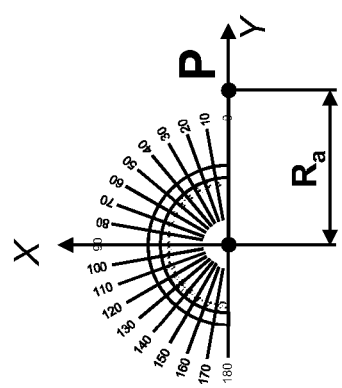
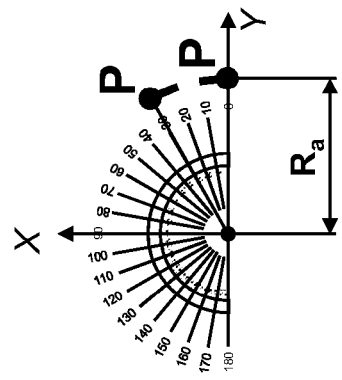
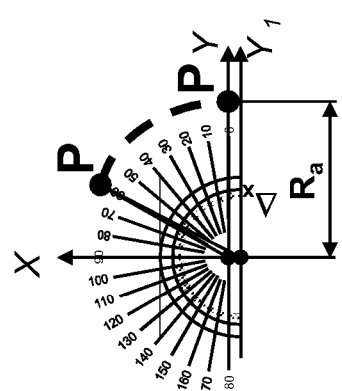
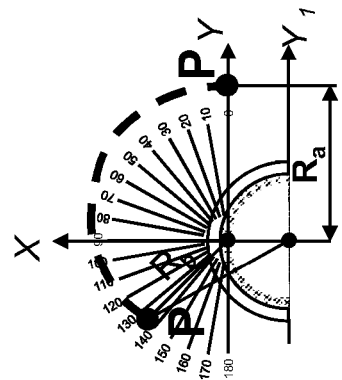
Fig. 4

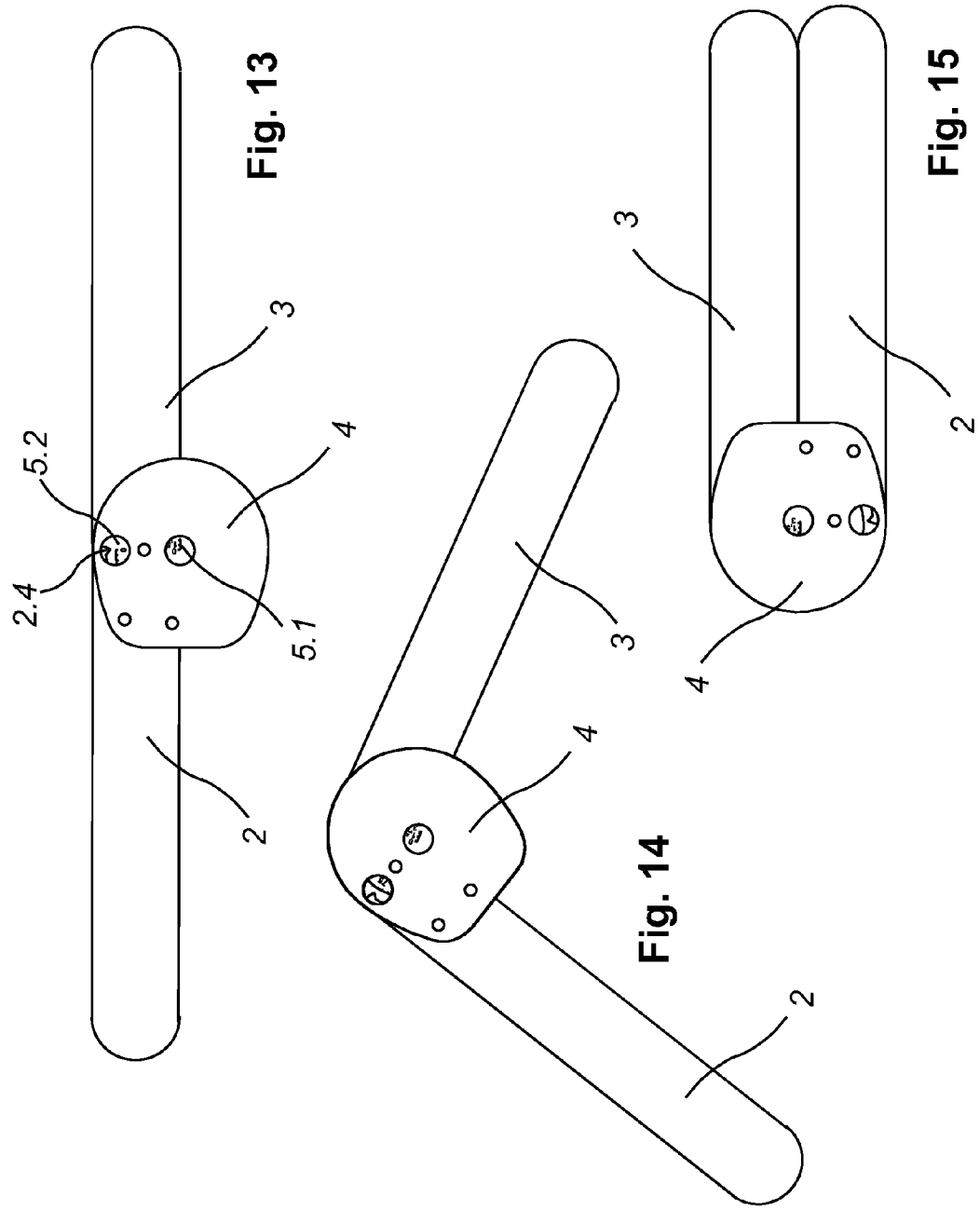

DEVICE FOR KNEE EVALUATION AND RELATIVE BRACE

TECHNICAL FIELD

The subject device is used in the medical field for a correct evaluation of the amplitude of movement of the knee. The joint shaped according to the device is used to make a brace for the knee sports.

BACKGROUND OF THE INVENTION

The movement of flexion of the knee occurs for the first 30 degrees according to a circular path around a fixed center during which the femoral condyle rolls on the tibial plateau. After this first phase, and then after 30 degrees the movement continues with a roto-translation phase characterized by the sliding ever more progressive of femoral condyle on the tibial plateau. Given the anatomical conformation of the condyle itself, this causes a progressive decrease of the distance between the instantaneous center of rotation and the articular surface. It is therefore evident there is a difference between the angle measured with a goniometric system and that really done from the knee, because in the phase of roto-translation the variation of the position of the center of rotation continuously changes spatial references of evaluation.

To make more explicit the above it is essential to consider a reference system X-Y in which the axis X coincides with the longitudinal axis tended limb that is, when the longitudinal axis of the thigh is in line with the longitudinal axis of the leg itself. The axis X intersects orthogonally Y and anatomically intersects horizontally the femoral condyle (FIG. 1). The initial center of rotation of the knee, and so, coincides with the origin of the Cartesian reference system X, Y.

For the evaluation of the movement amplitude of the knee it is therefore essential to provide a system which takes into account the displacement of the initial center of rotation during the roto-translational phase.

To describe the gradual shift of the axis of rotation of the knee, established that Ra is the first radius of rotation that lies on the axis Y, the trajectory of flexion-extension of the leg on the thigh is analytically defined:

for $\alpha < 30$ degrees knee motion is described as a rigid system that rotates around a fixed center: the trajectory performed by the point P has as equation that of a circle $X^2+Y^2=Ra^2$.

for 30 degrees $\leq \alpha < 135$ degrees, the center of rotation moves towards the articular surface of a quantity equal to $\Delta x$.

The new coordinates of point P become:

$$X1=X+\Delta_x$$

$$Y1=Y+\Delta_y$$

The equation of the center of rotation of the knee appears to be:

$$X1^2+Y1^2=Rb^2$$

where Rb is the real rotation radius that changes with the change of $\alpha$, with Rb<Ra When $\alpha$ is the angle between the axis X and the rotation radius, the values of X, X1, Y and Y1 are so obtained:

$$X=Ra\,\text{sen}\,\alpha$$

$$Y=Ra\cos\alpha$$

$$X1=Rb\,\text{sen}\,\alpha$$

$$Y1=Rb\cos\alpha$$

So for a given value of $\alpha$ between 30 and 135 degrees the position of the instantaneous center of rotation is calculated:

$$\Delta_x=X1-X=(Ra-Rb)\,\text{sen}\,\alpha$$

From 30 degrees of flexion onwards (135 degrees) the center of rotation, initially placed in the origin of the reference system, vertically slides towards the articular surface along the axis X by an amount equal to $\Delta_x$. The radius Ra remains unchanged in its length and drag the point P on a spiral path falling towards the center.

This determines that the distance between P and the origin of the reference system X-Y is reduced (Rb) (FIG. 2). After the 30 degrees, then, Rb whose first end is always centered in the origin of the reference system X, Y to the changing of $\alpha$ will assume different angular values of those of Ra which remains the actual radius of rotation of the knee.

From the above, it appears that in the roto-translational movement the point P placed at one end of the radius Ra follows a curve with a spiral path falling towards the center, while the first end of the radius Ra slides along the axis X. This implies that the scale for the evaluation of the real angle of the knee with reference to the radius Ra must be built according to the different movement of the two ends of radius Ra itself (FIGS. 3-4).

Several patents have faced the problem of roto-translational motion of the knee, but the applications were generally limited to application of mechanical devices to apply to the injured knee, restricting movement to an amplitude considered sufficient to second a "physiological" flexion of about 130 degrees, as necessary amplitude for a total recovery of functionality. Among these we cite the EP 0 361 405, the WO 84/03433, the WO 92/15264 and the WO 97/38759.

The knee joint described in the European Patent No. 0 361 405 is based on the physiological concept whereby the flexing of the knee consists in the fore movement of the femoral condyles with reference to the tibia condyles, followed by a sheer rotation between the condyles of the above mentioned bones. This joint features three plates, of which the two outer ones feature coaxial holes, while the inner one features two openings where a pair of pins that fit through the above mentioned holes in the outer plates are lodged and guided. One of the openings is small and extends transversally across the longitudinal axis of the tibia and femur, while the other opening is large and is shaped like a circular segment with one end growing wider towards the top.

The first opening, the transversal slot, has the function of reproducing the first fore movement of the femur with reference to the tibia, while the second opening serves the purpose of guiding the subsequent rotation movement.

The upper end of the circular opening is placed on the extension of the longitudinal axis of the arm of the central plate which passes through the centre of the pin lodged in the linear opening, precisely when the pin is halfway through the stroke performed by the pin inside this opening. The centre of the circular segment that constitutes the circular opening consists in the centre of the pin lodged in the linear opening when the pin itself is at the end of the said opening, which is the one farthest from the circular opening.

When the leg flexes, in the first 25° the pin lodged in the circular opening compels the pin in the linear opening to move from its starting position (closer to the circular opening) to its final position (at the end of the linear opening that lies farthest from the circular opening).

As the distance between the centres of the pins is equal to the radius of the circular opening, in this first part of the movement performed by the pin lodged in the linear opening, the pin lodged in the circular opening performs a small vertical movement within and outside the widened part that constitutes the upper part of the circular opening. In this first phase of the flexing movement the two outer plates slide forward with respect to the inner plate (traction or pulling apart phase of the two plates).

Subsequently the two outer plates rotate onto the inner one as the pin at the end of stroke position in the linear opening acts as a fulcrum and compels the pin lodged in the circular opening to move (sheer rolling phase).

The knee tutor joint described in the International Patent Application WO 84/03433 consists of five plates. The two outer ones, connected to the supporting elements of the lower leg, each feature a hole and a linear opening. The two intermediate plates also feature a hole and a linear opening each, but in the opposite position compared to the holes and openings of the outer plates.

The central plate, which is connected to the supporting elements of the upper leg, features a central hole and a bending opening which extends completely within the plate itself and which simulates the crosswise course of a flexing point on a given patient's knee.

The plates are locked onto one another and they can each pivot around one another and around the central shaft. This shaft extends through the linear openings in the outer plates and the central holes of the intermediate and central plates.

A pin passes through the peripheral holes of the two outer plates, the linear openings in the intermediate plates and the bending opening of the central plate. The central shaft and the pin lock the plates onto one another in such a way that the restricted movement of the pin inside the bending opening limits the movements of the supporting elements of the lower leg with respect to those of the upper leg: hence, the flexing and extension of the patient's lower leg is limited. The bending opening lodges some flexible pistons, which act as springs. These can move and are fastened to the ends of the bending opening in order to limit the movement of the pin and, consequently, the width of the flexing movement. These flexible pistons are locked by two threaded bolts next to each of which lies an indicator that moves longitudinally to the pistons themselves. The function of the indicators is to indicate the degrees of movement allowed in the flexing and extension movements: from 0° to 140°.

If one postulates that the central plate stays still, in this joint the intermediate plates rotate and move with respect to the central one. The outer plates rotate along with the intermediate ones but they move to the side of the latter plates along the axis in the direction of the linear openings in the intermediate and outer plates. In this system the outer plates move (rotate and slide) with respect to the central plate.

The central shaft and the pin that passes through the peripheral holes of the outer plates also change distance between them in the flexing movement.

However, there is no prior identification of the centre of the knee; this centre ought to be aligned with the central shaft. Furthermore, the possibility of personalising the bending opening is not described other than by referring to the extreme limits imposed on the movements.

The device described in the US2006/247565 proposes a pure circular motion with a goniometric system for setting the movement range. The joint is completed by two block systems for the extension and the flexion that can be located to several angles-shots. Such mechanical elements rotate around to a fixed center thus proposing only a partial reproduction of the physiological motion of the knee.

There are few patents which deals with a movement extends to larger degrees of freedom, even up to 150 and 160 degrees that is done in terms of prevention or that are able to support the knee of athletes in specific sports which occasionally undergo to particularly high loads that need, to be absorbed, a hyper-flexion of the knee. Among these we cite U.S. Pat. No. 4,643,176/A1.

Are further known US 2001/056012 and US 2005/148916.

Instead, we do not know of any patents that describe a measuring device of the actual angle reached by the knee in its phase of flexion. Today this evaluation occurs with the use of the traditional goniometer. The longitudinal axis of an arm is superimposed to the longitudinal axis of the thigh; the longitudinal axis of the other arm is superimposed to the longitudinal axis of the tibia. The center of rotation of the goniometer must be superimposed on the initial center of rotation of the knee in a way that the orthogonal axis to the rotation surfaces of the goniometer arms is coaxial with the transverse intercondylar rotation axis "c" of the knee itself But during the evaluation phase, after 30 degrees, the goniometer not proposing sliding between its two arms, that is what normally happens in the knee instead, is forced to let slide an arm on an anatomic segment. In fact, if we keep the instrument fixed to the thigh the goniometric distal arm moves relative to the leg, if we keep the instrument fixed to the leg the goniometric proximal arm moves relative to the thigh. This continual movement of the goniometer is not able to ensure that all the contact points remain constant from the beginning to the end of evaluation. This drawback let dropped the main feature to which must correspond an evaluation device, which is the possibility of the measurement repeatability.

And, always for the same reason, it is evident that also the notorious knee braces are not able to maintain during flexion the overlap of the longitudinal axis of their tibial arms with the longitudinal axis of the leg itself.

BRIEF SUMMARY OF THE INVENTION

The purpose of the present invention is to provide an evaluation device of the knee movement that lead the measurement and subsequent reading of the flexion extent at the knee taking into account of the translation after the 30 degrees.

Another object is to create a knee brace provided with a joint with a large flexion degree from 0 to 180 degrees and able to be used in prevention devices of the lateral tensions determined by particularly high tensions that are developed during specific sporting activities.

These and other objects are achieved by the subject device, comprising a first plate, a femoral arm, a tibial arm, a second plate and a small plate.

The first plate has a rounded shape and a first hole, a second hole, a third hole and a fourth hole.

The femoral arm consisting of a rectangular shaped blade which ends are particularly shaped. The distal end of the femoral arm is partially cut as quarter-circle and comprising a front distal sector and a rear distal sector. On the front distal sector an indicator is traced. The rear distal sector is shaped in a semicircle whose center is a first hole. A second hole is placed on an axis perpendicular to the rear edge passing through the center of the first hole of the femoral arm.

The tibial arm consisting in a rectangular shaped blade and a plate in a single body where the plate is the proximal end of the tibial arm. The tibial arm plate has a rounded shape and in the same lying a first tibial opening and a second tibial opening. The first tibial opening is rectangular in shape with rounded ends. The first tibial opening is achieved by creating a hole in the centre of the plate of the proximal end of the tibial arm and proceeding distally along an axis coaxial to the rear edge of the rectangular blade of the tibial arm. The second tibial opening is placed in a peripheral position on the proximal end of the tibial arm plate and extending for 180 degrees.

The second tibial opening for the first 25-30 degrees is an arc of a circle, for the next 105-110 degrees being a spiral coming inward towards the centre of the tibial arm plate and again being an arc of a circle from 135-140 degrees up to 180 degrees.

The proximal and rear peripheral edge of the plate constituting the proximal end of the tibial arm has a first part shaped as an arc of a circle, a second part being shaped as a spiral and a third part being shaped as an arc of a circle.

The second plate has a rounded shape and a first hole, a second hole, a third hole, a fourth hole and a fifth four hole. The second, fourth and fifth holes are threaded. The small plate is rounded shaped. On the small plate a linear scale and an angular graduate scale is traced. The small plate has a opening extending for 180 degrees. It is shaped as an arc of a circle for the first 25-30 degrees, for the next 105-110 degrees as a spiral and from 135-140 degrees up to 180 degrees as again an arc of a circle.

The proximal end of the tibial arm pivots on the first plate by a first pin and a second pin. The first pin is threaded at one end and the second pin has a through hole coaxial to its longitudinal axis. The first plate, which is placed in contact with the knee, is fixed to the distal end of the femoral arm and the second plate through three screws passing through the holes of the first plate and the holes of the femoral arm which are screwed in the threaded holes of the second plate. One of these screws passes through the hole of the second pin.

The first pin is screwed into the first hole of the first plate and is housed in the first tibial opening. An end of the second pin passes through the second tibial opening and is housed in the opening of the small plate. The height of the first pin is lower than height of the second pin and smaller than the thickness of the tibial arm.

Both the pins extend towards the plate constituting the proximal end of the tibial arm 3.

The group first plate—femoral arm—second plate—small plate is so joined with the plate constituting the proximal end of the tibial arm.

In accordance with a second aspect of the present invention the first plate includes a femoral arm which consists in a rectangular shaped blade and constitutes its distal end. The first plate has said first hole, second hole, third hole and fourth hole. The second plate has said first hole, second hole, third hole, fourth hole and fifth hole. On the semi-axis passes through the first and third holes of the second plate a reference indicator is made. on the circular small plate a linear scale and an angular graduate scale being traced.

The first pin, the second pin and a third pin extends between the first plate and second plate. The third pin has a through hole coaxial to its longitudinal axis which is passed by a first screw passing through the third hole of the first plate and is screwed in the threaded fourth hole of the second plate. The third pin is in contact with the rear peripheral edge of the plate constituting the proximal end of the tibial arm.

The brace for the knee presents two joints shaped according to the devices described above. The two femoral arms are connected by belts. Similarly the two tibial arms are connected by belts.

With the two holes in the second plate it is possible read the values in the two graduated scales traced on the small plate. This allows to evaluate the degree of flexion reached between the leg and thigh, for example, during a rehabilitation program, the evaluation reproposed in subsequent times, allows to see any improvements of joints compromised by the trauma and confirm the evolution of the healing process.

The device is then constructed by coupling a roto-translational movement a reading system consists of an angular scale modified and a linear scale for the measurement of the amounts of $\Delta_x$ understood as the approach of the center of rotation to the articular planes.

The angular variation on the new angular scale, therefore, no longer follows the law of rotation in the plane of an angle $\alpha$, but a combined effect of a rotation for 0 degrees<$\alpha$<30 degrees and of a roto-translation for 30 degrees≤$\alpha$<135 degrees. The division into notches on the graduated angular scale is not more regular as in a usual goniometer but it presents, over 30 degrees, a modified subdivision in function of axial translation.

In fact, considering that the end P of the radius Ra varies according to the following values:

$$Y1 = y$$

$$X1 = Ra \operatorname{sen} \alpha - \Delta_x$$

and observing two different readings on the scale (corresponding to different angles and at different $\Delta_x$ experimental in progressive values) we have:

$$X1_1 = Ra - \operatorname{sen} \alpha 1 - \Delta_{x1}$$

$$X2_1 = Ra - \operatorname{sen} \alpha 2 - \Delta_{x2}$$

So $$X1_1 - X2_1 = Ra(\alpha 1 \sin - \sin \alpha 2) - (\Delta_{x1} - \Delta_{x2})$$

From this report it is clear that this difference increases because $(\Delta_{x1} - \Delta_{x2})$ develops into discord to the X axis with consequent increase of the distance between two successive points of reading on the graduated angular scale.

The femoral arm of the subject device is approached to the thigh and the tibial arm to the leg. During the evaluation the tibial arm follows the roto-translational movement of the leg without slipping or remove itself. So, the device is able to maintain constant contact points from the beginning to the end of evaluation ensuring the repeatability.

The device allows to detect both the translation, by the value found on the linear scale and visible through the central hole of the second plate placed in correspondence with the linear scale itself, and the rotation through the value found on the angular graduated scale and visible through the peripheral hole of the second plate arranged at the same angular scale.

The actual value of the roto-translation of the knee is detectable by the different design of the angular graduated scale.

BRIEF DESCRIPTION OF DRAWINGS

Further characteristics of the invention will appear from the description of two forms of execution, preferred but not exclusive, of the device in question, illustrated by way of a non-limitative example in the accompanying drawings, in which:

FIG. 3 shows a femur and a tibia at various flexion degrees;

FIG. 4 shows the displacement of the reference point P on the axis X during the knee roto-translational motion;

FIG. 13 shows a front view of the evaluation device at 0 degrees (open);

FIG. 14 shows a front view of the evaluation device at 75 degrees;

FIG. 15 shows a front view of the evaluation device at 180 degrees (closed);

DETAILED DESCRIPTION OF TWO EMBODIMENTS

Figure 2:
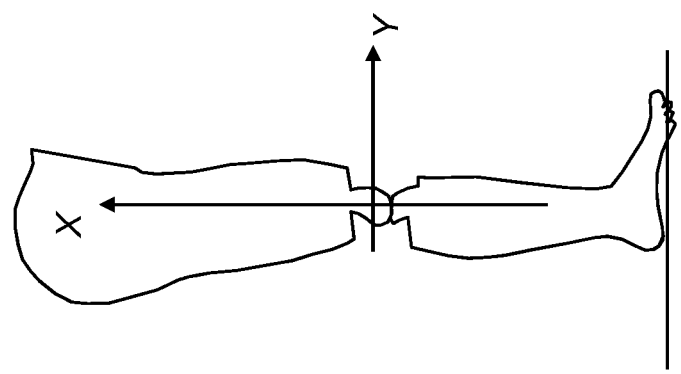
FIG. 2 shows a side view of a lower limb on which it has been reported a Cartesian reference which identifies the initial center of rotation of the knee.
Figure 1:
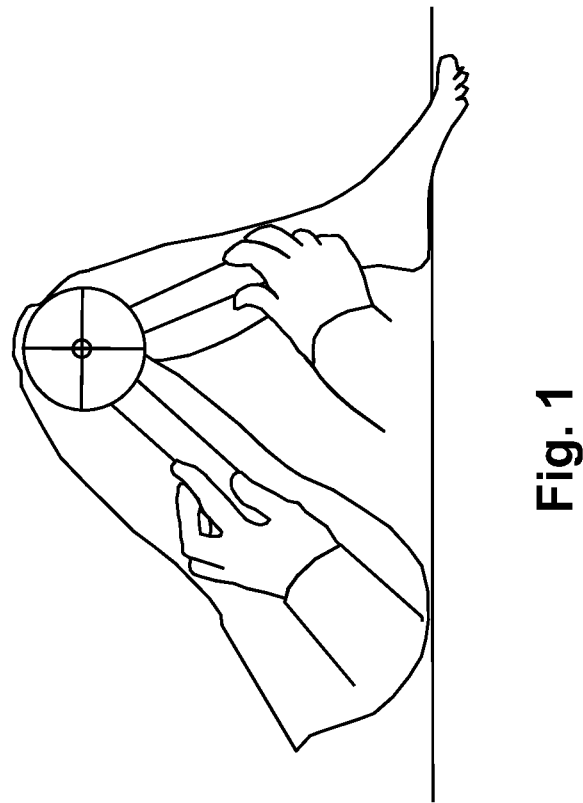
FIG. 1 shows a knee flexion evaluation by a usual goniometer.
Figure 6:
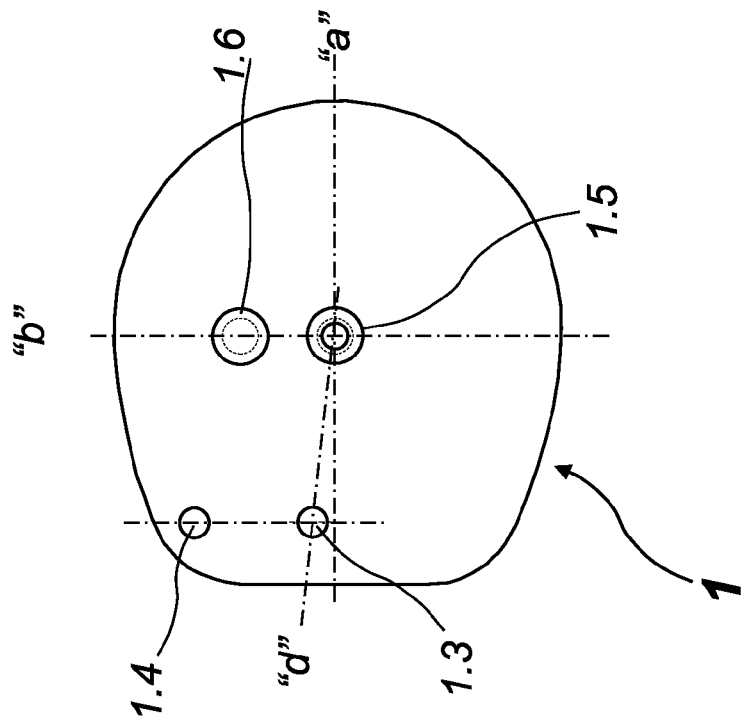
FIG. 6 shows a front view of the first plate provided with pins.
Figure 5:
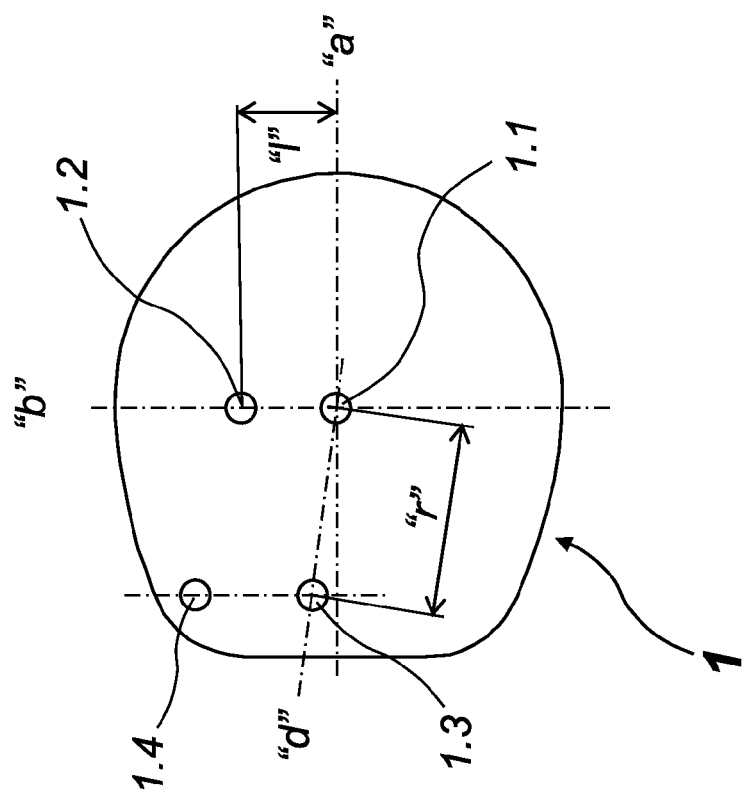
FIG. 5 shows a front view of a first plate of the device in a first form of execution.
Figure 7:
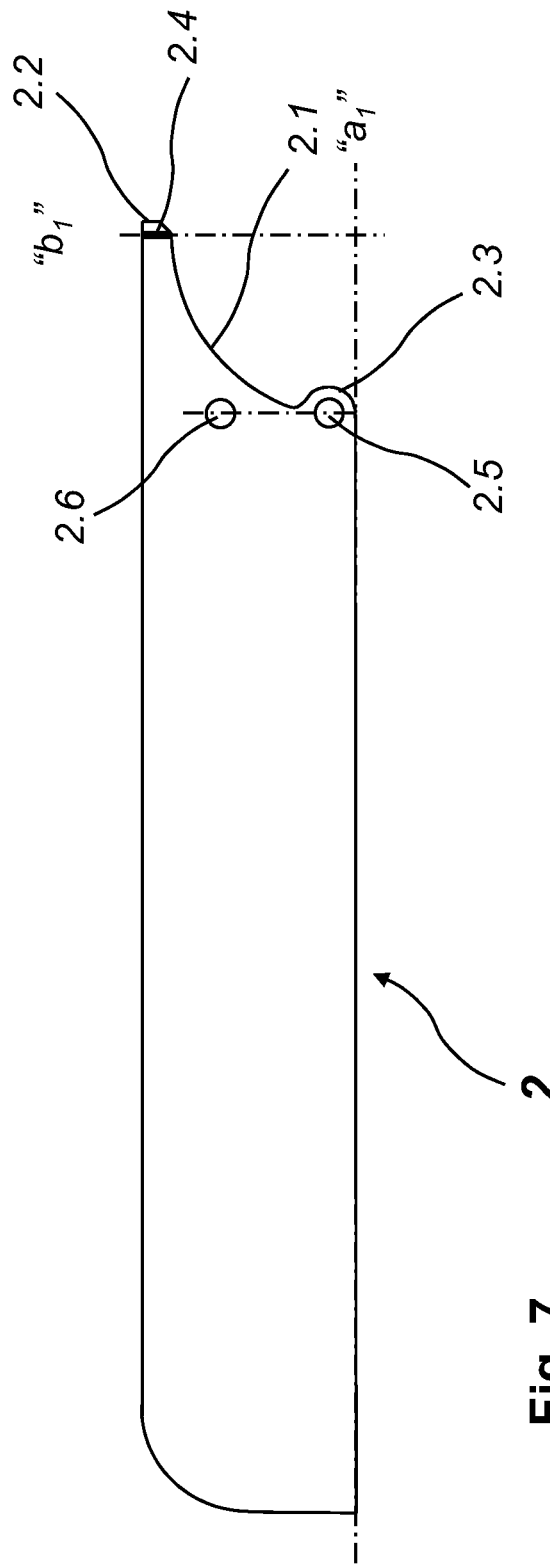
FIG. 7 shows a front view of the femoral arm in a first form of execution.
Figure 8:
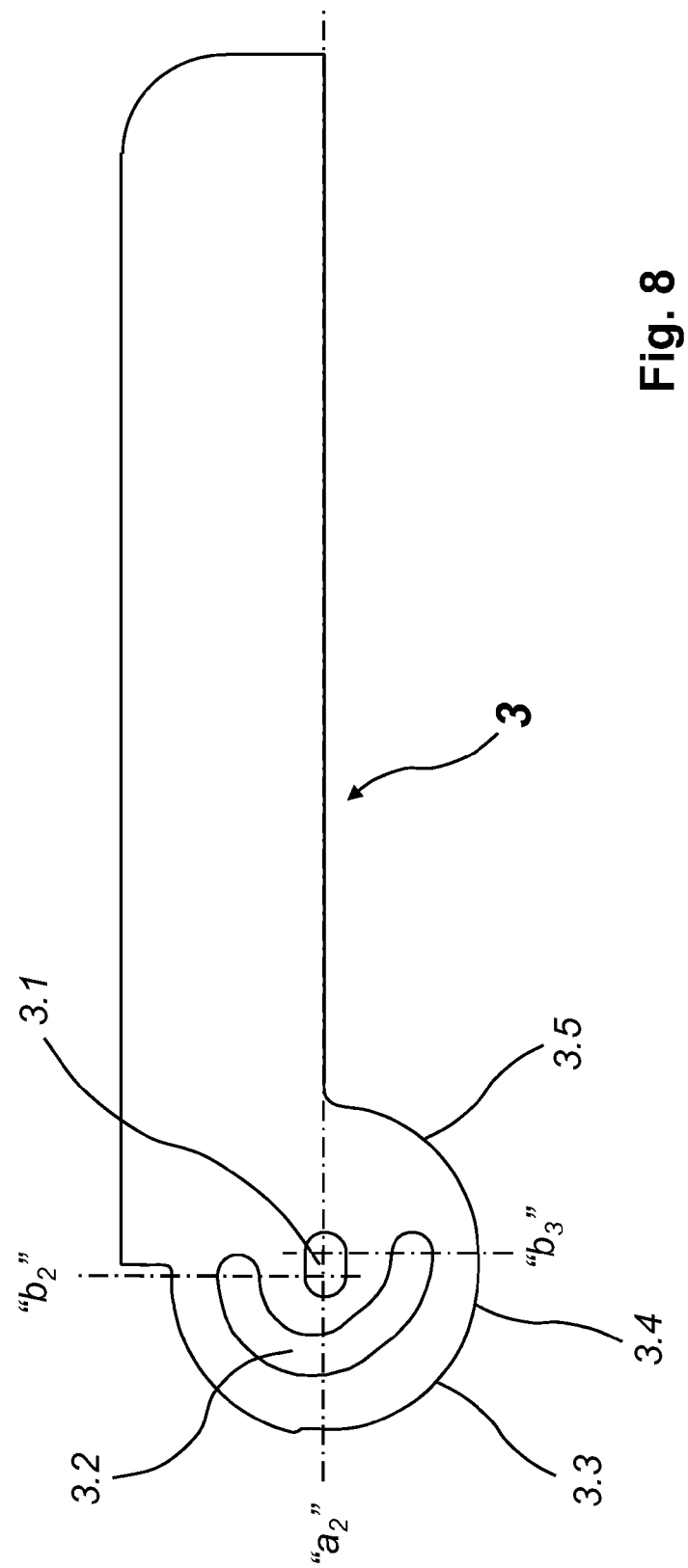
FIG. 8 shows a front view of the tibial arm.
Figure 9:
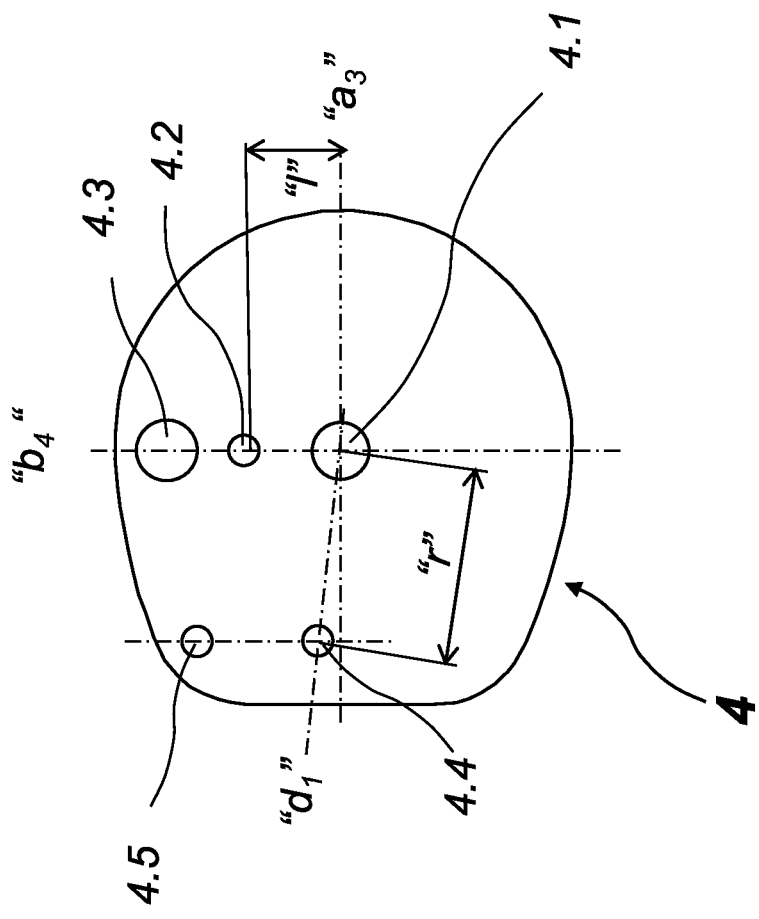
FIG. 9 shows a front view of a second plate in a first form of execution.
Figure 10:
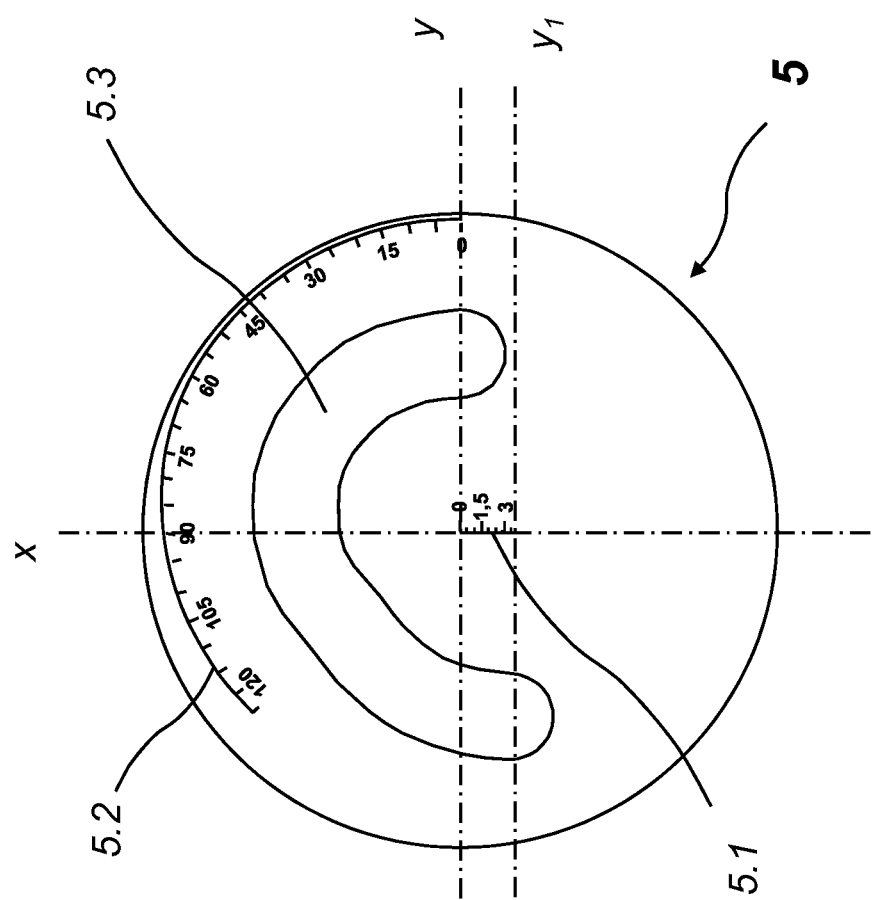
FIG. 10 shows a front view of a small plate provided with a linear scale and an angular scale.
Figure 11:
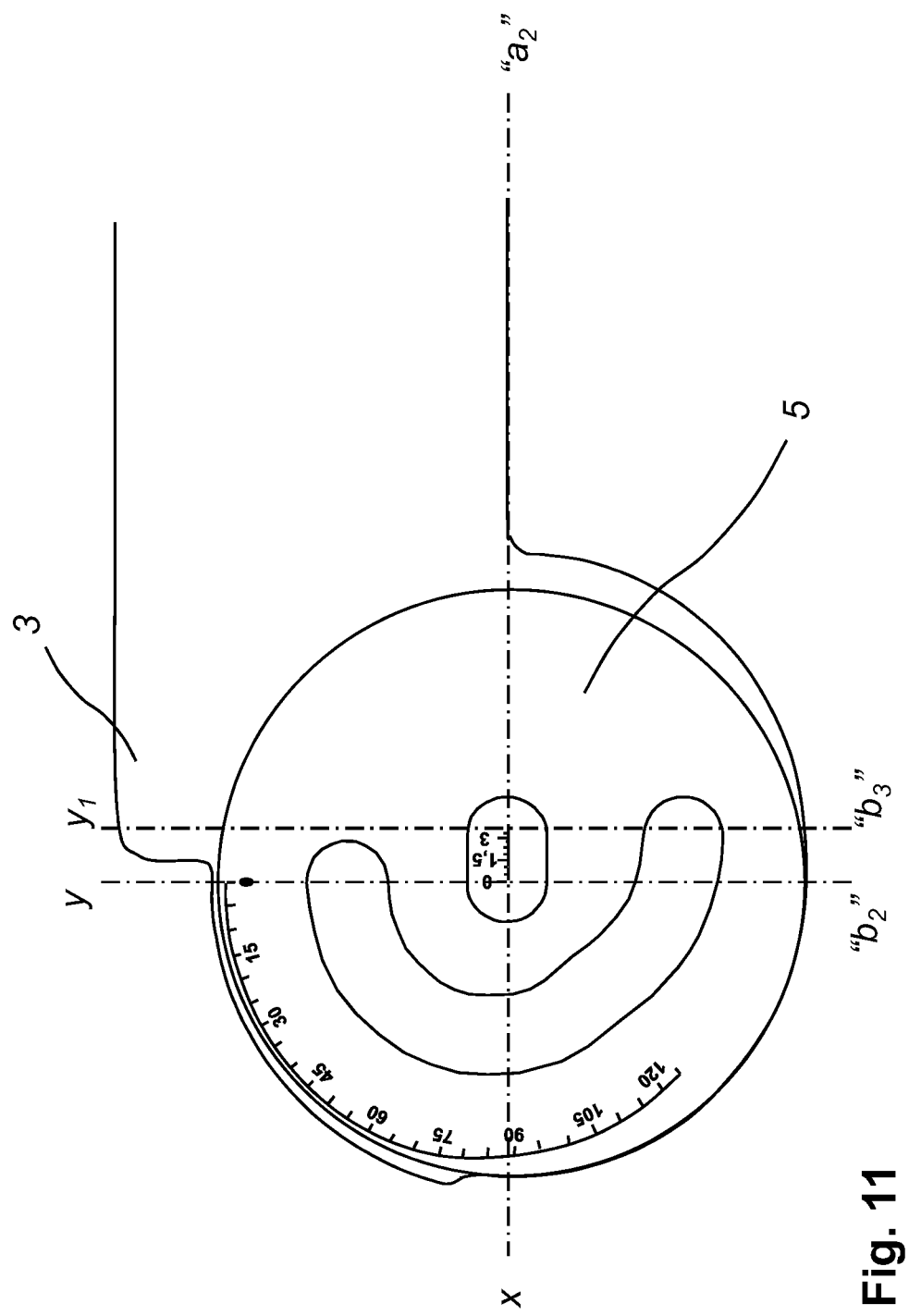
FIG. 11 shows a front view of the tibial arm and of the small plate superimposed to it.
Figure 12:
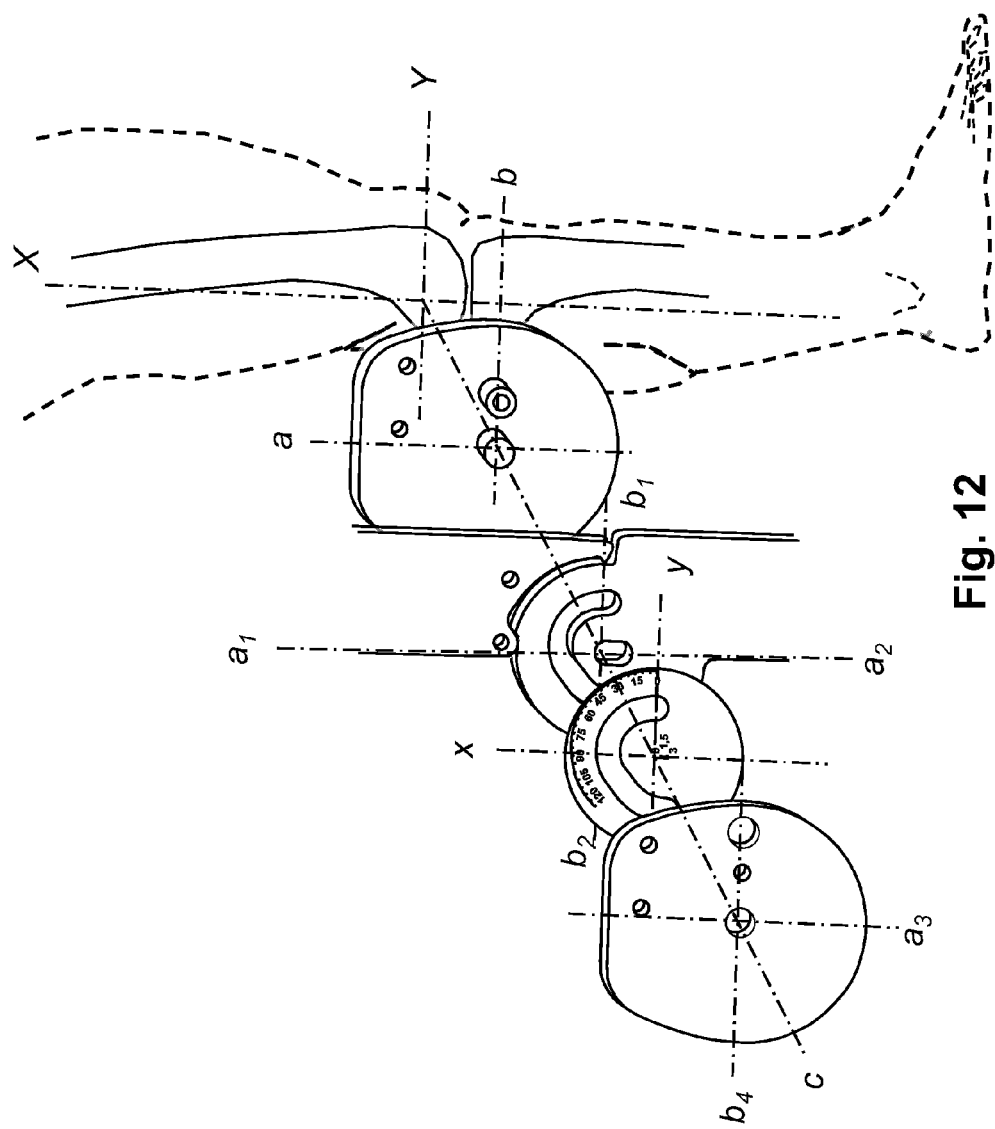
FIG. 12 shows an exploded view of the different elements of the device.

As shown in FIGS. 5-15 in a first embodiments the device for knee evaluation of the movement in question comprises a first plate 1, a femoral arm 2, a tibial arm 3, a second plate 4 and a small plate 5.

The first plate 1 has a rounded shape and a first hole 1.1, a second hole 1.2, a third hole 1.3 and a fourth hole 1.4.

The threaded first hole 1.1 is centrally located on the first plate 1 along a longitudinal axis "a" of the first plate 1.

The second hole 1.2 lies on the first plate 1 in a peripheral position along an axis "b" perpendicular to axis "a" passing through the first hole 1.1 of the first plate 1, and at a distance "l" with respect to the first hole 1.1 of the first plate 1.

Axis "a" and axis "b" allow to ideally divide the first plate 1 in four quadrant.

The third hole 1.3 is made on the first plate 1 at a distance "r" from the first hole 1.1 of the first plate 1 and located in the quadrant bounded by axis "a" and by the part of axis "b" on which the second hole 1.2 is made. The third hole 1.3 is positioned on the first plate 1 on a semi-axis "d" which departs by a few degrees from axis "a".

The fourth hole 1.4 is positioned on the first plate 1 on an axis perpendicular to axis "a" passing through the centre of the third hole 1.3 and located in the same quadrant.

The femoral arm 2 consists of a rectangular shaped blade which ends are particularly shaped. Specifically, the distal end is partially cut as quarter-circle and the centre of the cut part is located at the intersection between the rear edge of the femoral arm 2 and an axis "b1" orthogonal to such rear edge. The radius of the concavity 2.1 so formed is less than the length of the distal end of the femoral arm 2.

The distal end further comprises a front distal sector 2.2 and a rear distal sector 2.3. The concavity 2.1 is placed between the front distal sector 2.2 and the rear distal sector 2.3. The front distal sector 2.2 is orthogonal to the front edge. The axis "b1" is parallel to the front distal sector 2.2 and proximal to it.

On the front distal sector 2.2 an indicator 2.4 is traced, coinciding with axis "b1". The rear distal sector 2.3 of the concavity 2.1 is shaped in a semicircle whose centre is a first hole 2.5. A second hole 2.6 being placed on an axis perpendicular to the rear edge passing through the centre of the first hole 2.5.

The tibial arm 3 consists in a rectangular shaped blade and a plate in a single body where the plate is the proximal end of the tibial arm 3. The plate having an approximately rounded shape and in the same lie a first opening 3.1 and a second opening 3.2.

The first tibial opening 3.1 being rectangular in shape with rounded ends.

The first tibial opening 3.1 is achieved by creating a hole in the centre of the plate of the proximal end of the tibial arm 3 and proceeding distally along an axis "a2" coaxial to the rear edge of the rectangular blade of the tibial arm 3. The initial hole coincides so with the proximal end of the first tibial opening 3.1.

An axis "b2" passes through the centre of the proximal end of the first tibial opening 3.1; said axis "b2" is orthogonal to the axis "a2" of symmetry of the first tibial opening 3.1.

An axis "b3" passing through the centre of the distal end of the first tibial opening 3.1; said axis "b3" being orthogonal to the axis "a2" of symmetry of the tibial opening 3.1.

The second tibial opening 3.2 is placed in a peripheral position on the proximal end of the plate of the tibial arm 3 and extending to 180 degrees. A first end of said second tibial opening 3.2 is situated on said axis "b2" orthogonal to the axis of symmetry "a2" of the first tibial opening 3.1 towards the front edge of the plate. The first end of the second tibial opening 3.2 is placed at a distance "l" from the centre of the proximal end of the first tibial opening 3.1. The other end of the second tibial opening 3.2 lies on said axis "b3" towards the rear edge of the plate. The second tibial opening 3.2 has a specific form: for the first 25-30 degrees from said axis "b2" is an arc of a circle with its centre at the centre of the proximal end of the first tibial opening 3.1 and a radius equal to "l". Subsequently, for 105-110 degrees, is a spiral coming inward towards the centre of the plate. The longitudinal axis of this spiral derives from the sequence of points of the end of a segment of length "l" whose second end moves along the longitudinal axis "a2" of the first tibial opening 3.1 (proceeding from its proximal end to its distal end). From 135-140 degrees up to 180 degrees the second tibial opening 3.2 is again an arc of a circle with its centre coinciding with the centre of the distal end of the first tibial opening 3.1 and a radius equal to "l".

The proximal and rear peripheral edge of the plate constituting the proximal end of the tibial arm 3 is particularly shaped. In a first part 3.3 which starts in the proximal sector and develops in the rear sector the peripheral edge is shaped as an arc of a circle with the centre in the centre of the proximal end of the first tibial opening 3.1.

The first part 3.3 continues with a second part 3.4 which develops in the rear sector. In the second part 3.4 the peripheral edge is shaped as a spiral tending to move away from the centre of the plate constituting the proximal end of the tibial arm 3. More precisely, the points forming the longitudinal axis of this spiral are at a greater and greater distance from the centre of the proximal end of the first tibial opening 3.1.

The second part 3.4 continues with a third part 3.5. In the third part 3.5 the peripheral edge, which develops in the rear-distal sector is shaped as an arc of a circle with centre in the centre of the distal and of the first tibial opening 3.1.

The second plate 4 has a rounded shape. On the second plate a first hole 4.1, a second hole 4.2, a third hole 4.3, a fourth hole 4.4 an a fifth hole 4.5 are made.

The first hole 4.1 is centrally located on the second plate 4 along a longitudinal axis "a3" of the second plate 4. A second hole 4.2 lies on the second plate 4 along an axis "b4" orthogonal to axis "a3" and passing through the first hole 4.1, at a distance "l" with respect to the first hole 4.1.

Axis "a3" and axis "b4" ideally allowed to subdivide the second plate in four quadrants.

The third hole 4.3 is placed on the second plate 4 along an axis "b4" in a peripheral position from the second hole 4.2.

The fourth hole 4.4 is made on the second plate 4 at a distance "r" from the first hole 4.1. It is located in the quadrant bounded by axis "a3" and by the part of axis "b4" on which the second hole 4.2 and the third hole 4.3 are made. The fourth hole 4.4 is placed on a semi-axis "d1" which departs by a few degrees from axis "a3".

The fifth hole 4.5 is positioned, on the same quadrant of the second plate 4, on an axis orthogonal to axis "a3" passing through the centre of the fourth hole 4.4.

The second hole 4.2, the fourth hole 4.4 and the fifth hole 4.5 are threaded.

The small plate 5 is rounded shaped. On the circular small plate 5 a linear scale 5.1 and an angular graduated scale 5.2 is traced.

The linear scale 5.1 has a division in millimeters and is located along an axis x.

Said axis is intersected by an axis y, orthogonal to axis x.

The value 0 of the linear scale 5.1 coinciding with the intersection between axes x and y, and the values increase proceeding towards the periphery of the small plate 5.

Axis "x" and axis "y" ideally allow to subdivide the small plate 5 in four quadrants. The angular graduate scale 5.2 has value 0 degrees on axis y and extends counter clockwise in the diametrically opposite part to that in which the linear scale 5.1 extends.

The angular graduate scale 5.2 for the first 30 degrees follows a circular pattern and the angular distribution corresponds to the goniometric one; from 30 degrees on, the angular graduate scale 5.2 follows a spiral trend moving towards the centre with modification of the angular subdivision.

In detail, there is an increase between the distance between the notches proportional to the axial translation.

The small plate 5 with the double graduated scale has an opening 5.3 extending for 180 degrees. A first end of said opening 5.3 is located on axis y, at a distance from "l" from the intersection of axis "y" with axis "x" and towards value 0 degrees of the angular scale 5.2.

The second end of the opening 5.3 lies on an axis "y1" parallel to "y" and passing through the last value shown on the linear scale 5.1. The opening 5.3 has a specific form: for the first 25-30 degrees from the above-mentioned axis "y" is an arc of a circle has its centre at the intersection of axes x, y and has a radius equal to "1". Subsequently, for the next 105-110 degrees, is a spiral moving inward towards the intersection of axes x, y. The longitudinal axis of this spiral is derived from the sequence of points of the end of a segment of length "l" whose second end moves along the linear scale 5.1. From 135-140 degrees up to 180 degrees the shaped opening is again an arc of a circle has its centre coinciding with the last value shown on the linear scale 5.1 and a radius equal to "1".

In operation the distal part of the femoral arm 2 is superimposed on a part of the first plate 1 so that axis "a1" passing through the rear edge of the femoral arm 2 is parallel to longitudinal axis "a" of the first plate 1. The axis "a" coincides with the longitudinal axis of the thigh.

The axis "b1" parallel to the distal edge of the femoral arm 2 and proximal to it is parallel to axis "b" of the first plate 1.

The plate constituting the proximal end of the tibial arm 3 is superimposed on a part of the first plate 1 so that axis "a2" coaxial with the rear edge of the rectangular blade of the tibial arm 3 is parallel to longitudinal axis "a" of the first plate 1 and axis "b2" passes through the centre of the proximal end of the first tibial opening 3.1 is parallel to axis "b" of the first plate 1.

The first plate 1 is pivoted with the proximal end of the tibial arm 3 by a first pin 1.5 and a second pin 1.6. The first pin 1.5 is threaded at one end and the second pin 1.6 has a through hole coaxial to its longitudinal axis.

The tibial arm 3 is positioned distally to the femoral arm 2. The edge of the concavity 2.1 presents at the distal end of the femoral arm 2 always remaining in contact with the peripheral edge of the plate constituting the proximal end of the tibial arm 3 during movement of the tibial arm 3 in relation to the femoral arm 2. The small plate 5 is positioned on the plate constituting the proximal end of the tibial arm 3 aligning the intersection of axis "x" and axis "y" of the small plate 5 with the centre of the proximal end of the first tibial opening 3.1.

The axis "y", on which an indication is placed of the 0 degrees angle of the angular graduate scale 5.1, is coincident to axis "b2" passing through the centre of the proximal end of the first tibial opening 3.1. The last value shown on linear scale 5.1 coincides with the centre of the distal end of the first tibial opening 3.1. The opening 5.3 of the small plate 5 overlaps the second tibial opening 3.2.

The axis "y" of the small plate 5 is parallel to axis "a" of the first plate 1 and corresponds to the reference indicator 2.4 placed on the fore distal sector 2.2 of the femoral arm 2.

The second plate 4 is superimposed to the small plate 5, to the femoral arm 2 and to the tibial arm 3.

The axis "a3" of the second small plate 4 is parallel to axis "a1" of the femoral arm 2 and to axis "a2" of the tibial arm 3.

Axis "b4" of the second plate 4 is parallel to axis "b1" of the femoral arm 2 and to axis "b2" of the tibial arm 3.

The first plate 1 is fixed to the distal end of the femoral arm 2 and the second plate 4. In detail a first screw passing through the third hole 1.3 of the first plate 1 passes the first hole 2.5 of the femoral arm 2 and is screwed in the threaded fourth hole 4.4 of the second plate 4.

A second screw passing through the fourth hole 1.4 of the first plate 1 passes the second hole 2.6 of the femoral arm 2 and is screwed in the threaded fifth hole 4.5 of the second plate 4.

A third screw passing through the second hole 1.2 of the first plate 1 and the through hole of the second pin 1.6 is screwed in the threaded second hole 4.2 of the second plate 4.

An end of the second pin 1.6, after passing in through the second tibial opening 3.2, is housed in the opening 5.3 of the small plate 5.

The first pin 1.5 is screwed into the first hole 1.1 of the first plate 1 and is housed in the first tibial opening 3.1. Both the pins extend towards the plate constituting the proximal end of the tibial arm 3.

The first pin 1.5, the second pin 1.6, the first tibial openings 3.1 and the second tibial openings 3.2 form the movement mechanism of the device.

The pins 1.5, 1.6 allows the tibial arm 3 to freely move between the first plate 1 and the second plate 4. The height of the first pin 1.5 is lower to those of the second pin 1.6 and to the thickness of the tibial arm 3 so that the free end of the first pin 1.5 does not touch the small plate 5.

At the moment of the evaluation of knee movement the device is approached to the knee until the first plate 1 not going to touch it.

It is considered as a starting point for the evaluation the alignment between the femoral arm 2 and the tibial arm 3 which provides the extension between thigh and leg.

In this condition, the axis "a3" of the second plate 4, the axis "a1" which runs along the rear edge of the femoral arm 2 and the axis "a2" which runs along the rear edge of the rectangular blade of the tibial arm 3 are parallel with the longitudinal axis of the thigh and of the leg.

Always in this condition the axis "b4" placed on the second plate 4 is parallel to the axis "y" of the small plate 5 and coincides with the axis "b1" parallel to the distal edge of the front distal sector 2.2 of the femoral arm 2.

The value 0 degrees reported on the angular scale 5.2 is readable from the operator through the third hole 4.3 of the second plate 4.

At the same time the value 0 [mm] reported on the graduated linear scale 5.1 is readable through the first hole 4.1 present on the second plate 4.

As mentioned before the movement of knee flexion, for the first 30 degrees, takes place by rotation on a circular path around a fixed center. In this arc of movement the tibial arm 3 performs similarly an arc of a circle and more precisely:

the first pin 1.5 fixed on the first plate 1 rotates in correspondence of the center of the proximal end of the first tibial opening 3.1 of the tibial arm 3;

the second pin 1.6 slips in the first circular part of the second tibial opening 3.2;

the external edge of the rear distal sector 2.3 of the femoral arm 2 slips onto the first circular part 3.3 of the peripheral edge of the plate constituting the proximal end of the tibial arm 3.

The second phase of flexion between the leg and the thigh has an arc of movement from 30 to 135 degrees:

the first pin 1.5 fixed on the first plate 1 translates along the first opening 3.1;

the second pin 1.6 slips onto the part at spiral of the second tibial opening 3.2;

the external edge of the rear distal sector 2.3 of the femoral arm 2 slips onto the spiral second part 3.4 of the plate constituting the proximal end of the tibial arm 3.

The entity of the slip, is indicated on the linear graduated scale 5.1 placed on the small plate 5 and red through the first hole 4.1 of the second plate 4.

The entity of the flexion between the thigh and the leg, is indicated on the angular scale 5.2 placed on the small plate 5 and read through the first hole 4.3 of the second plate 4.

In this phase of knee movement the device of evaluation performs a rotary motion associated with a sliding more and more progressive similar to what happens between the articular heads.

During this second phase of the movement the device of evaluation remains perfectly in contact with the knee.

The different degrees of flexion reached are read on the angular scale 5.2 through the third hole 4.3 of the second plate 4. At the same time the different values of translation are readable on the linear graduated scale 5.1 through the first hole 4.1 of the second plate 4.

On the third phase of flexion from 135 to 180 degrees:

the first pin 1.5 fixed on the first plate 1 rotates in the distal end of the first tibial opening 3.1;

the second pin 1.6 slips into the third circular part of the second tibial opening 3.2;

the external edge of the rear distal sector 2.3 of the femoral arm 2 slips onto the rear-distal third circular part 3.5 of the plate constituting the proximal end of the tibial arm 3.

At the end of the flexion, the rear edge (coinciding with the axis "a1") of the femoral arm 2 and the rear edge (coinciding with the axis "a2") of the tibial arm 3 are facing.

In this arc of flexion, the movement does not occur in a voluntary way, but only if assisted or forced.

In fact the articular physiology at the closed angle between femur and tibia, determines a conflict between the rear portion of the tibial plate and the rear/upper portion of the femoral condyle with great tension of the cruciate ligaments.

In the field of rehabilitation a forcing situation is operated in a passive manner and it becomes an indicator of ligament iper-laxity possibly favored by ipotrofismo of the muscles of the lower limb.

In sports, instead, hyperflexion at angles greater than 135-140 degrees are the result of tensions generated by the specificity of sport. For example, during ski an irregularity of the ground is able to create a force, proportional to the weight of the skier and to the speed of advance, which exhausts towards the center of gravity of the athlete who, in order to absorb this tension, is forced to an hyperflexion of the lower limbs, even for a very short time.

The movement phase from 135 to 180 degrees also allows to close and store the device, reducing its size, after making the necessary measurements.

In a second form of execution the device has substantially the same elements of the first form of execution. It will therefore be described only the substantial differences of the same.

Figure 16:
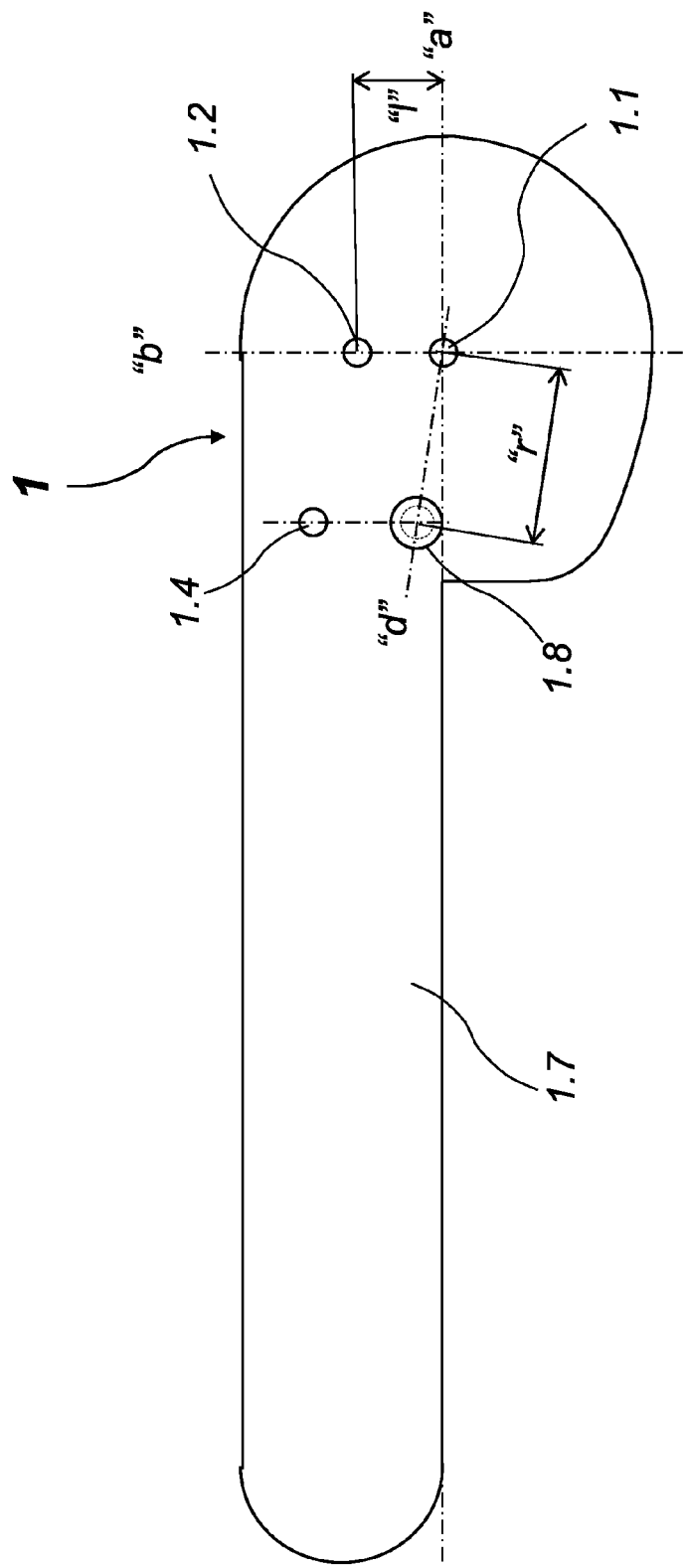
FIG. 16 shows a front view of the first plate of the device in a second form of execution.
Figure 17:
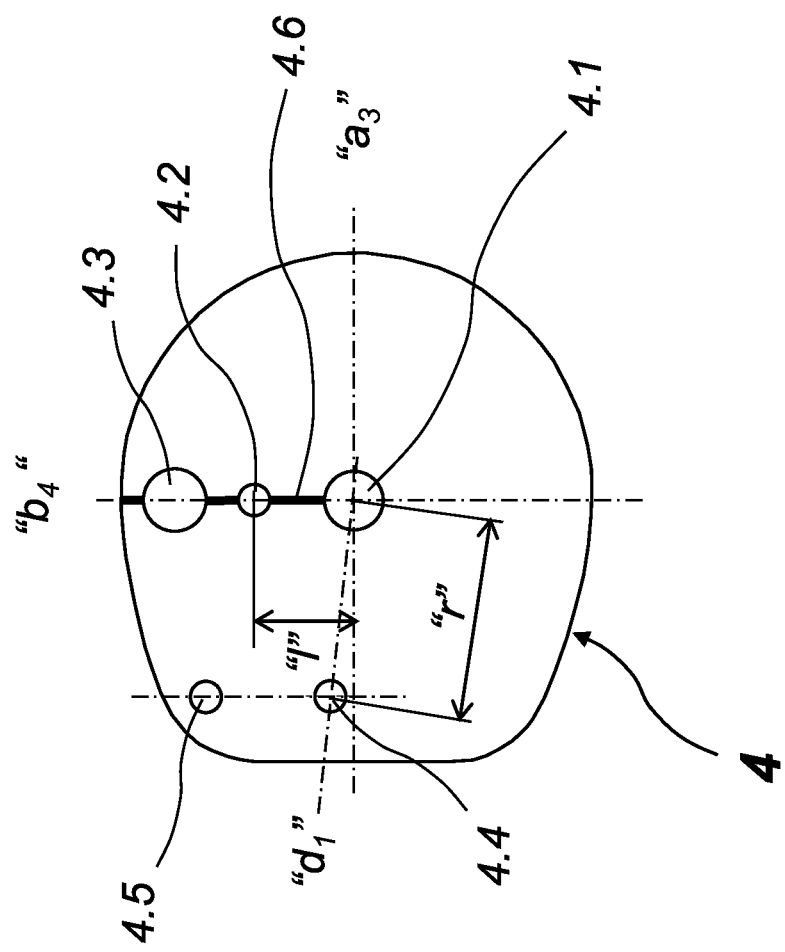
FIG. 17 shows a front view of the second plate of the device in a second form of execution.

Referring now to FIGS. 16, 17 there is shown a device according to a second embodiment of the present invention. The first plate 1 has a femoral arm 1.7 which is rectangular shaped. The first plate 1 is the distal end of the femoral arm 1.7. On the first plate 1 are present the above mentioned first hole 1.1, second hole 1.2, third hole 1.3 and fourth four hole 1.4.

The axis "a" passing for the first hole 1.1, is coaxial to the rear edge of the femoral arm 1.7.

The second plate 4 has rounded shape. On the second plate 4 are realized the above-mentioned first hole 4.1, second hole 4.2, third hole 4.3, fourth hole 4.4 and fifth hole 4.5. On the semi axis "b4" passing for the first and third hole 4.1, 4.3 of the second plate 4 is realized a reference indicator 4.6.

The first pin 1.5, the second pin 1.6 and a third pin 1.8 extend between the first plate 1 and second plate 4. The third pin 1.8 has a through hole coaxial to its longitudinal axis which is passed by the first screw which passes the third hole 1.3 of the first plate 1 too and is screwed in the fourth hole 4.4 of the second plate 4. The tibial arm 3 is superimposed at a part of the first plate 1. The third pin 1.8 is in contact with the rear peripheral edge of the plate constituting the proximal end of the tibial arm 3.

The invention claimed is:

1. Device for knee evaluation, comprising:
a first plate having a rounded shape and a first hole, a second hole, a third hole and a fourth hole; said first hole of the first plate being threaded and being centrally located along a longitudinal axis ("a") of the first plate; said second hole of the first plate being in a peripheral position and lying along an axis ("b") perpendicular to axis ("a") passing through the first hole of said first plate; said second hole being at a distance "l" with respect to the first hole of said first plate; said third hole being on the first plate at a distance "r" from the first hole; the third hole being located in the quadrant bounded by axis ("a") and by the part of axis ("b") on which the second hole of said first plate lying; said third hole of said first plate being positioned on a semiaxis ("d"), which departs by a few degrees from axis ("a"); said fourth hole being positioned on an axis perpendicular to axis ("a") passing through the centre of the third hole of said first plate and located in the same quadrant;
a femoral arm consisting in a rectangular shaped blade which ends being particularly shaped; the distal end of the femoral arm is partially cut as quarter-circle and the centre of the cut part being located at the intersection between the rear edge of the femoral arm and an axis ("b1") orthogonal to the rear edge of the femoral arm; the radius of the concavity so formed is less than the length of the distal end of the femoral arm; the distal end said femoral arm further comprising a front distal sector and a rear distal sector; the concavity is placed between the front distal sector and the rear distal sector; the front distal sector is orthogonal to the front edge of said femoral arm; the axis "b1" being parallel to the front distal sector and proximal to it; a reference indicator being traced on the front distal sector; said reference indicator coinciding with axis ("b1"); the rear distal sector of the concavity being shaped in a semicircle whose centre is a first hole of said femoral arm; a second hole of said femoral arm being placed on an axis perpendicular to the rear edge of the femoral arm passing through the centre of the first hole of the femoral arm;

a tibial arm consisting in a rectangular shaped blade and a plate in a single body where the plate being the proximal end of the tibial arm; said tibial arm plate having a rounded shape and in the same lying a first opening and a second opening; said first tibial opening being rectangular in shape with rounded ends and is achieved by creating a hole in the centre of the plate of the proximal end of the tibial arm and proceeding distally along an axis ("a2") coaxial to the rear edge of the rectangular blade of the tibial arm; the initial hole coincides with the proximal end of the first tibial opening; an axis ("b2") passing through the centre of the proximal end of the first tibial opening and an axis ("b3") passing through the centre of the distal end of the first tibial opening; said axes ("b2", "b3") being orthogonal to the axis of symmetry of the first tibial opening; said second tibial opening being placed in a peripheral position on the proximal end of the plate of the tibial arm and extending for 180 degrees; a first end of said second tibial opening being situated on said axis ("b2"), towards the front edge of the plate of the tibial arm and at a distance "l" from the centre of the proximal end of the first tibial opening; the other end of the second tibial opening lying on said axis ("b3") towards the rear edge of the plate of the tibial arm; said second tibial opening for the first 25-30 degrees from said axis ("b2") being an arc of a circle with its centre at the centre of the proximal end of the first tibial opening and a radius equal to "l"; said second tibial opening for the next 105-110 degrees being a spiral coming inward towards the centre of the tibial arm plate; the longitudinal axis of this spiral being derived from the sequence of points of the end of a segment of length "l" whose second end moves along the longitudinal axis ("a2") of the first tibial opening proceeding from its proximal end to its distal end; said second tibial opening being again an arc of a circumference from 135-140 degrees up to 180 degrees with its centre coinciding with the centre of the distal end of the first tibial opening and a radius equal to "l"; the proximal and rear peripheral edge of the plate constituting the proximal end of tibial arm having a first part which starts in the proximal sector and develops in the rear sector the peripheral edge being shaped as an arc of a circle with the centre in the centre of the proximal end of the first tibial opening; the first part of the peripheral edge of the plate constituting the proximal end of tibial arm continuing with a second part which develops in the rear sector; the second part of the peripheral edge being shaped as a spiral tending to move away from the centre of the plate constituting the proximal end of the tibial arm; the points forming the longitudinal axis of this spiral are at a greater and greater distance from the centre of the proximal end of the first tibial opening; the second part continues with a third part which develops in the rear-distal sector; the third part of the peripheral edge being shaped as an arc of a circle with centre in the centre of the distal and of the first tibial opening;

a second plate having a rounded shape and a first hole, a second hole, a third hole, a fourth hole and a fifth hole; said first hole of the second plate being centrally located along a longitudinal axis ("a3") of the second plate; the second hole of the second plate lying along an axis ("b4") perpendicular to axis ("a3") and passing through the first hole of the second plate, at a distance "l" with respect to the first hole of the second plate; the third hole of the second plate being placed along axis ("b4") in a peripheral position from the second hole of the second plate; the fourth hole being made on the second plate at a distance "r" from the first hole of the second plate and located in the quadrant bounded by axis ("a3") and by the part of axis ("b4") on which the second and the third holes of the second plate being made; the fourth hole being positioned on a semiaxis "d1" which departs by a few degrees from axis ("a3"); the fifth hole of the second plate being positioned on an axis perpendicular to axis ("a3") passing through the centre of the fourth hole of the second plate located in the same quadrant; said second hole, fourth hole and fifth hole being threaded;

a rounded shaped small plate; on the small plate a linear scale and an angular graduate scale being traced; said linear scale having a division in millimeters and being located along an axis "x" intersected by an axis "y", orthogonal to axis "x"; the value 0 of the linear scale coinciding with the intersection between axes "x" and "y", and the values increase proceeding towards the periphery of the small plate; said angular graduate scale having value 0 degrees on axis "y" and extends on the small plate counterclockwise in the diametrically opposite part to that in which the linear scale extending; the angular graduate scale for the first 30 degrees follows a circular pattern and the angular distribution corresponds to the goniometric one; from 30 degrees on, the angular graduate scale follows a spiral trend moving towards the centre with an increase in the distance between the notches proportional to axial displacement; said small plate having an opening extending for 180 degrees, a first end of which being located on axis "y" at a distance "l" from the intersection of axis "y" with axis "x" and towards value 0 degrees of the angular scale; the other end of the small plate opening lying on an axis "y1" parallel to "y" and passing through the last value shown on the linear scale; said small plate opening for the first 25-30 degrees from the above-mentioned axis "y" being an arc of a circle having its centre at the intersection of axes "x" and "y" and having a radius equal to "l"; said small plate opening for the next 105-110 degrees being a spiral moving inward towards the intersection of axes "x" and "y"; the longitudinal axis of this spiral deriving from the sequence of points of the end of a segment of length "l" whose second end moves along said linear scale; said small plate opening from 135-140 degrees up to 180 degrees being again an arc of a circle having its centre coinciding with the last value shown on the linear scale and a radius equal to "l";

the distal part of the femoral arm being superimposed on a part of the first plate so that axis ("a1") passing through the rear edge of the femoral arm being parallel to longitudinal axis ("a") of the first plate) and axis ("b1") parallel to the distal edge of the femoral arm and proximal to it being parallel to axis ("b") of the first plate; the plate forming the proximal end of the tibial arm being superimposed on a part of the first plate so that axis ("a2") coaxial with the rear edge of the rectangular blade of the tibial arm being parallel to longitudinal axis ("a") of the first plate and axis ("b2") passing through the centre of the proximal end of the first tibial opening being parallel to axis ("b") of the first plate; said tibial arm being positioned distally to the femoral arm; the edge of the above-mentioned concavity always remaining in contact with the peripheral edge of the proximal end of the plate forming the proximal end of the tibial arm during movement of the latter in relation to the femoral arm; said small plate being positioned on the plate forming the proximal end of the tibial arm aligning the intersection of axis "x" and axis "y" of the small plate with the centre of the proximal end of the first tibial opening; axis "y", on which an indication being placed of the 0 degrees angle of the angular graduate scale, being parallel to axis ("b2") passing through the centre of the proximal end of the first tibial opening; the last value shown on linear scale coincides with the centre of the distal end of the first tibial opening and the small plate opening overlaps the second tibial opening; axis "y" of the small plate being parallel to axis ("a") of the first plate and corresponds to the reference indicator placed on the fore distal end of the femoral arm; the second plate being then superimposed on the small plate, on the femoral arm and on the tibial arm; axis ("a3") of the second plate being parallel to axis ("a1") of the femoral arm and to axis ("a2") of the tibial arm; axis ("b4") of the second plate being parallel to axis ("b1") of the femoral arm and to axis ("b2") of the tibial arm; said proximal end of the tibial arm being pivoted by a first pin and a second pin to the first plate; said first pin being threaded at one end and the second pin having a through hole coaxial to its longitudinal axis; said first pin being screwed into the first hole of the first plate and being housed in the first tibial opening; said first plate being fixed with the distal end of the femoral arm and the second plate through three screws; a first screw passing through the third hole of the first plate passes the first hole of the femoral arm and being screwed in the threaded fourth hole of the second plate; a second screw passing through the fourth hole of the first plate passes the second hole of the femoral arm and being screwed in the threaded fifth hole of the second plate; a third screw passing through the second hole of the first plate and the through hole of the second pin being screwed in the threaded second hole of the second plate; an end of the second pin, after passing through the second tibial opening, being housed in the small plate opening; the height of the first pin being lower than the height of the second pin and smaller than the thickness of the tibial arm; the first pin and the second pin extending towards the plate constituting the proximal end of the tibial arm; the group first plate—femoral arm—second plate—small plate being so joined with the proximal end of the tibial arm.

2. The device for knee evaluation according to claim 1, characterized for comprising two joints according to the device described above; the two femoral arms are connected by belts; the two tibial arms are connected by belts.

3. Device for knee evaluation, comprising:
a first plate having a rounded shape and a first hole, a second hole, a third hole and a fourth hole; said first hole of the first plate being threaded and being centrally located along a longitudinal axis ("a") of the first plate; said second hole of the first plate being in a peripheral position and lying along an axis ("b") perpendicular to axis ("a") passing through the first hole of said first plate; said second hole being at a distance "l" with respect to the first hole of said first plate; said third hole being on the first plate at a distance "r" from the first hole; the third hole being located in the quadrant bounded by axis ("a") and by the part of axis ("b") on which the second hole of said first plate lying; said third hole of said first plate being positioned on a semiaxis ("d"), which departs by a few degrees from axis ("a"); said fourth hole being positioned on an axis perpendicular to axis ("a") passing through the centre of the third hole of said first plate and located in the same quadrant;

a femoral arm consisting in a rectangular shaped blade integral with the first plate; the first plate constituting the distal end of the femoral arm; the axis ("a") passing through the first hole of the first plate being coaxial with the rear edge of the femoral arm;

a tibial arm consisting in a rectangular shaped blade and a plate in a single body where the plate being the proximal end of the tibial arm; said tibial arm plate having a rounded shape and in the same lying a first opening and a second opening; said first tibial opening being rectangular in shape with rounded ends and is achieved by creating a hole in the centre of the plate of the proximal end of the tibial arm and proceeding distally along an axis ("a2") coaxial to the rear edge of the rectangular blade of the tibial arm; the initial hole coincides with the proximal end of the first tibial opening; an axis ("b2") passing through the centre of the proximal end of the first tibial opening and an axis ("b3") passing through the centre of the distal end of the first tibial opening; said axes ("b2", "b3") being orthogonal to the axis of symmetry of the first tibial opening; said second tibial opening being placed in a peripheral position on the proximal end of the plate of the tibial arm and extending for 180 degrees; a first end of said second tibial opening being situated on said axis ("b2"), towards the front edge of the plate of the tibial arm and at a distance "l" from the centre of the proximal end of the first tibial opening; the other end of the second tibial opening lying on said axis ("b3") towards the rear edge of the plate of the tibial arm; said second tibial opening for the first 25-30 degrees from said axis ("b2") being an arc of a circle with its centre at the centre of the proximal end of the first tibial opening and a radius equal to "l"; said second tibial opening for the next 105-110 degrees being a spiral coming inward towards the centre of the tibial arm plate; the longitudinal axis of this spiral being derived from the sequence of points of the end of a segment of length "l" whose second end moves along the longitudinal axis ("a2") of the first tibial opening proceeding from its proximal end to its distal end; said second tibial opening being again an arc of a circumference from 135-140 degrees up to 180 degrees with its centre coinciding with the centre of the distal end of the first tibial opening and a radius equal to "l"; the proximal and rear peripheral edge of the plate constituting the proximal end of tibial arm having a first part which starts in the proximal sector and develops in the rear sector the peripheral edge being shaped as an arc of a circle with the centre in the centre of the proximal end of the first tibial opening; the first part of the peripheral edge of the plate constituting the proximal end of tibial arm continuing with a second part which develops in the rear sector; the second part of the peripheral edge being shaped as a spiral tending to move away from the centre of the plate constituting the proximal end of the tibial arm; the points forming the longitudinal axis of this spiral are at a greater and greater distance from the centre of the proximal end of the first tibial opening; the second part continues with a third part which develops in the rear-distal sector; the third part of the peripheral edge being shaped as an arc of a circle with centre in the centre of the distal and of the first tibial opening;

a second plate having a rounded shape and a first hole, a second hole, a third hole, a fourth hole and a fifth hole; said first hole of the second plate being centrally located along a longitudinal axis ("a3") of the second plate; the second hole of the second plate lying along an axis ("b4") perpendicular to axis ("a3") and passing through the first hole of the second plate, at a distance "l" with respect to the first hole of the second plate; the third hole of the second plate being placed along axis ("b4") in a peripheral position from the second hole of the second plate; the fourth hole being made on the second plate at a distance "r" from the first hole of the second plate and located in the quadrant bounded by axis ("a3") and by the part of axis ("b4") on which the second and the third holes of the second plate being made; the fourth hole being positioned on a semiaxis "d1" which departs by a few degrees from axis ("a3"); the fifth hole of the second plate being positioned on an axis perpendicular to axis ("a3") passing through the centre of the fourth hole of the second plate located in the same quadrant; said second hole, fourth hole and fifth hole being threaded; on the axis ("b4") passing through the first and third holes of the second plate a reference indicator being made;

a rounded shaped small plate; on the small plate a linear scale and an angular graduate scale being traced; said linear scale having a division in millimeters and being located along an axis "x" intersected by an axis "y", orthogonal to axis "x"; the value 0 of the linear scale coinciding with the intersection between axes "x" and "y", and the values increase proceeding towards the periphery of the small plate; said angular graduate scale having value 0 degrees on axis "y" and extends on the small plate counterclockwise in the diametrically opposite part to that in which the linear scale extending; the angular graduate scale for the first 30 degrees follows a circular pattern and the angular distribution corresponds to the goniometric one; from 30 degrees on, the angular graduate scale follows a spiral trend moving towards the centre with an increase in the distance between the notches proportional to axial displacement; said small plate having an opening extending for 180 degrees, a first end of which being located on axis "y" at a distance "l" from the intersection of axis "y" with axis "x" and towards value 0 degrees of the angular scale; the other end of the small plate opening lying on an axis "y1" parallel to "y" and passing through the last value shown on the linear scale; said small plate opening for the first 25-30 degrees from the above-mentioned axis "y" being an arc of a circle having its centre at the intersection of axes "x" and "y" and having a radius equal to "l"; said small plate opening for the next 105-110 degrees being a spiral moving inward towards the intersection of axes "x" and "y"; the longitudinal axis of this spiral deriving from the sequence of points of the end of a segment of length "l" whose second end moves along said linear scale; said small plate opening from 135-140 degrees up to 180 degrees being again an arc of a circle having its centre coinciding with the last value shown on the linear scale and a radius equal to "l"; the plate forming the proximal end of the tibial arm being superimposed on the first plate constituting the distal end of the femoral arm so that axis ("a2") coaxial with the rear edge of the rectangular blade of the tibial arm being parallel to longitudinal axis ("a") of the first plate coaxial with the rear edge of the femoral arm; axis ("b2") passing through the centre of the proximal end of the first tibial opening being parallel to axis ("b") of the first plate of the distal end of the femoral arm; said tibial arm being positioned distally to the femoral arm; said small plate being positioned on the plate forming the proximal end of the tibial arm aligning the intersection of axis "x" and axis "y" of the small plate with the centre of the proximal end of the first tibial opening; axis "y", on which an indication being placed of the 0 degrees angle of the angular graduate scale, being parallel to axis ("b2") passing through the centre of the proximal end of the first tibial opening; the last value shown on linear scale coincides with the centre of the distal end of the first tibial opening and the small plate opening overlaps the second tibial opening; axis "y" of the small plate being parallel to axis ("b") of the first plate constituting the distal end of the femoral arm and corresponds to the reference indicator placed on the second plate; the second plate being then superimposed on the small plate, on the first plate constituting the distal end of the femoral arm and on the tibial arm; axis ("a3") of the second plate being parallel to axis ("a") of the first plate constituting the distal end of the femoral arm and to axis ("a2") of the tibial arm; axis ("b4") of the second plate being parallel to axis ("b") of the first plate constituting the distal end of the femoral arm and to axis ("b2") of the tibial arm; said proximal end of the tibial arm being pivoted by a first pin and a second pin to the first plate constituting the distal end of the femoral arm; said first pin being threaded at one end and the second pin having a through hole coaxial to its longitudinal axis; said first plate constituting the distal end of the femoral arm being fixed with the second plate through three screws; a first screw passing through the third hole of the first plate passes through the third pin having a through hole coaxial to its longitudinal axis; said first screw being screwed in the threaded fourth hole of the second plate; a second screw passing through the fourth hole of the first plate constituting the distal end of the femoral arm being screwed in the threaded fifth hole of the second plate; a third screw passing through the second hole of the first plate constituting the distal end of the femoral arm and the through hole of the second pin being screwed in the threaded second hole of the second plate; an end of the second pin, after passing through the second tibial opening, being housed in the small plate opening; said first pin being screwed into the first threaded hole of the first plate constituting the distal end of the femoral arm and being housed in the first tibial opening; the group first plate of the femoral arm—second plate— small plate being so joined with the proximal end of the tibial arm; the third pin being in contact with the rear peripheral edge of the plate constituting the proximal end of the tibial arm.

4. The device for knee evaluation according to claim 3, characterized for comprising two joints according to the device described above; the two femoral arms are connected by belts; the two tibial arms are connected by belts.

* * * * *